United States Patent [19]

Bruserud et al.

[11] Patent Number: 5,770,190
[45] Date of Patent: Jun. 23, 1998

[54] METHOD OF TREATMENT OF ACUTE LEUKEMIA WITH INTELEUKIN-10

[75] Inventors: Øystein Bruserud, Eidsvåg, Norway; Mary Ellen M. Rybak, Warren, N.J.

[73] Assignee: Schering Corporation, Kenilworth, N.J.

[21] Appl. No.: 670,298

[22] Filed: Jun. 27, 1996

[51] Int. Cl.$^6$ .................................................. A61K 45/05
[52] U.S. Cl. ........................ 424/85.2; 424/85.1; 530/351
[58] Field of Search ................................. 424/85.1, 85.2; 530/351

[56] References Cited

FOREIGN PATENT DOCUMENTS

| | | |
|---|---|---|
| WO 91/00349 | 1/1991 | WIPO. |
| WO 92/12725 | 8/1992 | WIPO. |
| WO 92/12726 | 8/1992 | WIPO. |
| WO 94/04180 | 3/1994 | WIPO. |

OTHER PUBLICATIONS

Goselink et al., Blood, vol. 80 (3), pp. 750–757, 1992.
fluckiger et al. J. Cellular Biochem., Suppl. 0 vol. 16 part C, p. 74, 1992.
Finke et al. , 1993, Leukemia, 7(11):1852–1857 (Abstr.).
Fluckiger et al., 1994, *The Journal of Experimental Medicine*, 179:91–99.
Geissler et al., 1995, *Blood*, 86:664A.

*Primary Examiner*—Chhaya D. Sayala
*Attorney, Agent, or Firm*—Cynthia L. Foulke; Norman C. Dulak

[57] ABSTRACT

A method is provided for treating acute leukemias, e.g. acute myelogenous leukemia and acute lymphocytic leukemia. The method comprises administering to a mammal a therapeutically effective amount of interleukin-10.

16 Claims, 6 Drawing Sheets

METHOD OF TREATMENT OF ACUTE LEUKEMIA WITH INTELEUKIN-10

This application claims priority to provisional application No. 60/001,159, filed Jul. 14, 1995.

FIELD OF THE INVENTION

This invention relates to the use of interleukin-10 (IL-10) to treat acute leukemias, such as acute myelogenous leukemia (AML) and acute lymphocytic leukemia (ALL).

BACKGROUND OF THE INVENTION

AML and ALL are acute leukemias that can result in death within a matter of only months without effective treatment. See, e.g., *Harrison's Priniciples of Internal Medicine,* 12th ed. (1991), pp. 1552–1561, McGraw Hill, N.Y., N.Y. Wilson et al. (eds.). The AML diagnosis is based on the morphological recognition of an increased number of immature leukemia blast cells in the bone marrow. See Bennet etal., Br. J. Hematol. 33:451 (1976). The AML blast cells may also show various morphological signs of differentiation, including morphological characteristics similar to mature monocytes/macrophages. See Id. The ALL diagnosis is based on light microscopy, biochemistry and membrane molecule analysis. See, e.g., *Clinical Medicine,* Vol. 5, Chapter 16, Spittell (ed.) Harper & Row, Philadelphia, Pa. (1986).

Although AML and ALL are both acute leukemias, each represents a different disease, differing in natural history, prognosis, and response to various therapeutic agents. See, e.g., *Harrison's Priniciples of Internal Medicine,* 12th ed. (1991), pp. 1552–1561, McGraw Hill, N.Y., N.Y. Wilson et al. (eds.). For instance, AML and ALL have different epidemiological profiles (AML being more common in adults than in children), different cytogenetic changes, different malignant transformation requirements, and different patterns of response to specific chemotherapeutic agents. In addition, AML and ALL affect hematopoietic progenitor cells at different stages.

Recently, there has been progress in immunologic approaches to cancer therapy. These approaches are based on the notion that cancer cells have somehow evaded the body's defenses against aberrant or foreign cells and molecules, and that these defenses might be therapeutically stimulated to attack the cancer cells. See e.g., pgs. 623–648 in Klein, *Immunology* (Wiley-Interscience, New York, 1982). Immunologic approaches to cancer therapy have received renewed interest in view of recent observations that various immune effectors can directly or indirectly inhibit tumor growth. See, e.g, Herberman, *Concepts Immunopathol.,* Vol. 1, pgs. 96–132 (1985) (natural killer cells resist tumor cell growth); Rosenberg et al., *Ann. Rev. Immunol.,* Vol. 4, pgs. 681–709 (1988) (clinical use of IL-2-activated killer cells to treat cancer); Ralph et al., *J. Exp. Med.,* Vol. 167, pgs. 712–717 (1988) (tumoricidal activity by macrophages stimulated by lymphokines); Tepper et al., *Cell,* Vol 57, pgs 503–512 (1989) (IL-4 has anti-tumor activity); M. Cohen, *"Lymphokines and the Immune Response"* (CRC Press, Boca Raton, 1990); and the like.

Recent data support the use of one particular immune effector, Interleukin-10 (IL-10), to treat neoplastic conditions. See, e.g., International Patent Application Publications WO 92/12725 and WO 92/12726. Furthermore, several studies have demonstrated that IL-10 has an immunosuppressive effect on normal monocytes and thereby influences the function of other immunocompetent cells. See, e.g., de Waal Malefyt et al., Curr. Opin. Immunol. 4: 314 (1992); Yssel et al., *J. Exp. Med.* 174: 593 (1991); Fiorentimo et al., *J. Immunol.* 147:3815 (1991); and de Waal Malefyt et al., *J. Exp. Med.* 174: 1209 (1991).

However, notwithstanding the wide variety of advances in immunologic approaches to cancer therapy, there remains a great need for methods of treating acute leukemias such as AML and ALL.

SUMMARY OF THE INVENTION

This invention fills the foregoing needs by providing a method for treating an acute leukemia in a mammal, comprising administering a therapeutically effective amount of interleukin-10 to said mammal. This invention also provides a method for inhibiting proliferation of acute leukemia blast cells comprising administering a therapeutically effective dose of interleukin-10 to a mammal suffering from an acute leukemia.

Further, the present inventors have surprisingly found that this antiproliferative effect of IL-10 persists even after administration of the IL-10 is stopped. Accordingly, this invention also provides a method for treating an acute leukemia in a mammal, comprising administering a therapeutically effective amount of interleukin-10 to said mammal, wherein the interleukin-10 has an antiproliferative effect on acute leukemia blast cells which persists after the administration of interleukin-10 is stopped.

In accordance with the methods of the present invention, the acute leukemia to be treated can be a myeloid cell leukemia such as acute myelogenous leukemia (AML) or a B cell leukemia such as acute lymphocytic leukemia (ALL). The IL-10 to be administered can be selected from the group consisting of viral interleukin-10 and human interleukin-10.

BRIEF DESCRIPTION OF THE FIGURES

This invention can be more readily understood by reference to the accompanying figures, in which:

FIGS. 2A, 2B, 2C, and 2D are graphical representations showing the effect of IL-10 (10 ng/ml) on spontaneous and cytokine-dependent AML blast proliferation. In each figure, the vertical axis measures proliferation as shown by $^3$H-thymidine incorporation. However, the horizontal axis does not represent incremental measurements. Rather, the data points corresponding to the left side of the horizontal axis represent proliferation without IL-10, while the data points corresponding to the right side of the horizontal axis represent proliferation with IL-10. The results for each of these figures are presented as median cpm of triplicate cultures.

FIGS. 3A and 3B are graphical representations showing the effect of IL-10 (20 ng/ml) on spontaneous and cytokine-dependent AML blast proliferation for Patient No. 2 (FIG. 3A) and Patient No. 15 (FIG. 3B). AML blasts were cultured with IL-10 either throughout the whole culture period (unshaded bars) or only for the first 48 hours and thereafter cultured without IL-10 (shaded bars). The AML blasts were cultured in medium alone (Sp) or together with haematopoietic growth factors (G-CSF, GM-CSF, IL-3). For cells preincubated in IL-10 the growth factors were added after 48 hours, whereas growth factors were added together with IL-10 when IL-10 was present throughout the whole culture period. Proliferation was assayed as $^3$H-thymidine incorporation after 7 days of culture. The results are presented as the relative response (RR) defined as proliferation in cultures containing IL-10 relative to proliferation in corresponding cultures without IL-10. All cultures were performed in triplicates, and the median cpm was used to calculate the relative response.

DETAILED DESCRIPTION OF THE INVENTION

All references cited herein are hereby incorporated in their entirety by reference.

As used herein, "interleukin-10" or "IL-10" is defined as a protein which (a) has an amino acid sequence of mature IL-10 (e.g., lacking a secretory leader sequence) as disclosed in U.S. Pat. No. 5,231,012 and (b) has biological activity that is common to native IL-10. For the purposes of this invention both glycosylated (e.g. produced in eukaryotic cells such as CHO cells) and unglycosylated (e.g., chemically synthesized or produced in E. coli) IL-10 are equivalent and can be used interchangeably. Also included are muteins and other analogs, including the Epstein-Barr Virus protein BCRF1 (viral IL-10), which retain the biological activity of IL-10.

IL-10 suitable for use in the invention can be obtained from culture medium conditioned by activated cells secreting the protein, and purified by standard methods. Additionally, the IL-10, or active fragments thereof, can be chemically synthesized using standard techniques known in the art. See Merrifield, Science 233: 341 (1986) and Atherton et al., *Solid Phase Peptide Synthesis: A Practical Approach*, 1989, I.R.L. Press, Oxford. See also U.S. Pat. No. 5,231,012.

Preferably, the protein or polypeptide is obtained by recombinant techniques using isolated nucleic acid encoding the IL-10 polypeptide. General methods of molecular biology are described, e.g., by Sambrook et al., *Molecular Cloning, A Laboratory Manual*, Cold Spring Harbor, N.Y., 2d ed., 1989, and by Ausubel et al., (eds.) *Current Protocols in Molecular Biology*, Green/Woley, N.Y. (1987 and periodic supplements). The appropriate sequences can be obtained using standard techniques from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, e.g., U.S. Pat. No. 5,231,012, which discloses recombinant methods for making IL-10. Useful gene sequences can be found, e.g., in various sequence databases, e.g., GenBank and BMPL or nucleic acid and PIR and Swiss-Prot for protein, c/o Intelligenetics, Mountain View, Calif., or the Genetics Computer Group, University of Wisconsin Biotechnology Center, Madison, Wis.

Clones comprising sequences that encode human IL-10 have been deposited with the American Type Culture Collection (ATCC), Rockville, Md., under Accession Nos. 68191 and 68192. Identification of other clones harboring the sequences encoding IL-10 is performed by either nucleic acid hybridization or immunological detection of the encoded protein, if an expression vector is used. Oligonucleotide probes based on the deposited sequences disclosed in U.S. Pat. No. 5,231,012 are particularly useful. Oligonucleotide probes sequences can also be prepared from conserved regions of related genes in other species. Alternatively, degenerate probes based on the amino acid sequences of IL-10 can be used.

Standard methods can be used to produce transformed prokaryotic, mammalian, yeast or insect cell lines which express large quantities of the polypeptide. Exemplary *E. coli* strains suitable for both expression and cloning include W3110 (ATCC Bi, 27325), X1776 (ATCC No. 31244). X2282, and RR1 (ATCC Mp/31343). Exemplary mammalian cell lines include COS-7 cells, mouse L cells and CHP cells. See Sambrook (1989), supra and Ausubel et al., 1987 supplements, supra.

Various expression vectors can be used to express DNA encoding IL-10. Conventional vectors used for expression of recombinant proteins in prokaryotic or eukaryotic cells may be used. Preferred vectors include the pcD vectors described by Okayama et al., Mol. Cell. Biol. 3: 280 (1983); and Takebe et al., Mol. Cell. Biol. 8: 466 (1988). Other SV40-based mammalian expression vectors include those disclosed in Kaufman et al., Mol. Cell. Biol. 2: 1304 (1982) and U.S. Pat. No. 4,675,285. These SV40-based vectors are particularly useful in COS-7 monkey cells (ATCC No. CRL 1651), as well as in other mammalian cells such as mouse L cells. See also, Pouwels et al., (1989 and supplements) *Cloning Vectors: A Laboratory Manual*, Elsevier, N.Y.

The IL-10 may be produced in soluble form, such as a secreted product of transformed or transfected yeast, insect or mammalian cells. The peptides can then be purified by standard procedures that are known in the art. For example, purification steps could include ammonium sulfate precipitation, ion exchange chromatography, gel filtration, electrophoresis, affinity chromatography, and the like. See *Methods in Enzymology Purification Principles and Practices* (Springer-Verlag, N.Y., 1982).

Alternatively, IL-10 may be produced in insoluble form, such as aggregates or inclusion bodies. The IL-10 in such a form is purified by standard procedures that are well known in the art. Examples of purification steps include separating the inclusion bodies from disrupted host cells by centrifugation, and then solubilizing the inclusion bodies with chaotropic agent and reducing agent so that the peptide assumes a biologically active conformation. For specifics of these procedures, see, e.g. Winkler et al., Biochemistry 25:

4041 (1986), Winkler et al., Bio/Technology 3: 9923 (1985); Koths et al., and U.S. Pat. No. 4,569,790.

The nucleotide sequences used to transfect the host cells can be modified using standard techniques to make IL-10 or fragments thereof with a variety of desired properties. Such modified IL-10 can vary from the naturally-occurring sequences at the primary structure level, e.g., by amino acid, insertions, substitutions, deletions and fusions. These modifications can be used in a number of combinations to produce the final modified protein chain.

The amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylated variants or proteins which are conjugated to polyethylene glycol (PEG), etc. Such variants can be used in this invention as long as they retain the biological activity of IL-10.

Modifications of the sequences encoding the polypeptides may be readily accomplished by a variety of techniques, such as site-directed mutagenesis (Gillman et al., Gene 8: 81 (1987)). Most modifications are evaluated by routine screening in a suitable assay for the desired characteristics. For instance, U.S. Pat. No. 5,231,012 describes a number of in vitro assays suitable for measuring IL-10 activity.

Preferably, human IL-10 is used for the treatment of humans, although viral or mouse IL-10, or IL-10 from some other mammalian species, could possibly be used. Most preferably, the IL-10 used is recombinant human IL-10. The preparation of human and mouse IL-10 has been described in U.S. Pat. No. 5,231,012. The cloning and expression of viral IL-10 (BCRF1 protein) from Epstein-Barr virus has been disclosed by Moore et al., Science 248: 1230 (1990).

When referring to IL-10, active fragments thereof, analogs and homologs are included. Active fragments, analogs and homologs to IL-10 include those proteins, polypeptides, or peptides which possess one or more various characteristic IL-10 activities. Any of these proteinaceous entities can be glycosylated or unglycosylated. Examples of IL-10 activity include inhibition or substantial reduction of the level of IL-2, lymphotoxin, IL-3, or GM-CSF. IL-10 activity also includes inhibition of cytokine production by activated macrophages, e.g., IL-1, IL-6, and TNF-$\alpha$.

For examples of procedures and assays to determine IL-10 activity, see U.S. Pat. No. 5,231,012. This patent also provides proteins having IL-10 activity and production of such proteins including recombinant and synthetic techniques.

To prepare pharmaceutical compositions including polypeptide IL-10, the polypeptide is admixed with a pharmaceutically acceptable carrier or excipient which is preferably inert. A pharmaceutical carrier can be any compatible non-toxic substance suitable for delivery of the polypeptide to a patient. Preparation of such pharmaceutical compositions is known in the art; see, e.g., *Remington's Pharmaceutical Sciences, and U.S. Pharmacopeia: National Formulary*, Mack Publishing Company, Easton, Pa. (1984).

The proportion of polypeptide and additive can be varied over a broad range so long as both are present in therapeutically effective amounts. On a per-dose basis, the amount of the peptide could range from about 1 microgram ($\mu$g) to about 10 milligrams (mg).

Compositions may be ingested orally or injected into the body. Formulations for oral use include compounds to protect the polypeptides from proteases which occur in the gastrointestinal tract. Injections are usually intramuscular, subcutaneous, intradermal or intravenous. Alternatively, intra-articular injection or other routes could be used in appropriate circumstances.

When administered parenterally, the compositions can be formulated in a unit dosage injectable form (solution, suspension, emulsion) in association with a pharmaceutical carrier. For instance, the polypeptide may be administered in aqueous vehicles such as water, saline or buffered vehicles with or without various additives and/or diluting agents. Examples of suitable carriers are normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. However, the IL-10 is preferably formulated in purified form substantially free of aggregates and other proteins. In addition, it should be noted that a suspension, such as a zinc suspension, can be prepared to include the polypeptide. Such a suspension can be useful for subcutaneous (SQ) or intramuscular (IM) injection.

As used herein, the phrase "therapeutically effective amount" means an amount sufficient to ameliorate a symptom or sign of an acute leukemia. Both AML and ALL are defined as an increase of blast cells in the bone marrow to >30% of the nucleated cells. Symptoms and clinical signs can differ among individual patients. A worsening of the clinical status during cytokine therapy could be, e.g., increasing fever, increasing bone marrow failure, increasing number of blast cells in peripheral blood or bone marrow. When the effect of AML therapy is evaluated, this is done usually by investigating bone marrow and peripheral blood values. AML and ALL can be considered ameliorated or in partial remission when there is a greater than 50% reduction of bone marrow blasts and a reduction of peripheral blood counts such that transfusion dependence is decreased even though the number of counts is less than normal. A complete remission to therapy in cases of AML and ALL is often defined as normal cellularity of the bone marrow with less than 5% blasts, and in addition normal peripheral blood counts for granulocytes and thrombocytes.

Typical mammals that can be treated include companion animals such as dogs and cats, and primates, including humans. Preferably, IL-10 derived from the species of the treatment target animal will be used. An effective amount for a particular patient may vary depending on factors such as the condition being treated, the overall health of the patient, the method, route, and dose of administration and the severity of side effects. Determination of the appropriate dose is made by the clinician using parameters known in the art. Generally, the dose begins with an amount somewhat less than the optimum dose and it is increased by small increments thereafter until the desired or optimum effect is achieved. (See generally *The Merck Manual* § 269 "Pharmacokinetics and Drug Administration.").

In view of in vitro data described below showing an increase in blast cell proliferation for a minority of AML patients, care must obviously be taken to monitor whether patients undergoing treatment with IL-10 exhibit an increase in blast cell proliferation. As a further precaution, prospective patients can first be screened by, e.g., in vitro testing. The methods described in the examples below can be used for this purpose. For instance, as shown in the examples below, suitable in vitro testing could comprise removing leukemic blast cells from the patient, culturing the cells in vitro with and without IL-10, measuring cell proliferation, and comparing proliferation by the cells cultured with IL-10 against proliferation by the cells cultured without IL-10. In this method, measurement of proliferation can be accomplished, e.g., by assaying for $^3$H-thymidine incorporation in accordance with the methods described in the Examples below. As an alternative way to screen patients, colony formation or effects on cytokine secretion could be tested with and without the presence of IL-10.

The preferred total daily dose of IL-10 is selected from a range of about 1 microgram to about 500 micrograms per kilogram of body weight. More preferably, the therapeutically effective amount is selected from a range of about 10 micrograms to about 200 micrograms per kilogram of body weight. Most preferably, the therapeutically effective amount is selected from a range of about 25 micrograms to about 100 micrograms per kilogram of body weight. Dosages are on a schedule which effects the desired treatment and can be periodic over short or longer term. The daily infusion rate may be varied based on monitoring of side effects, blood cell counts, and efficacy. See Gilman et al. (eds.) (1990) *Goodman and Gilman's: The Pharmacological Bases of Therapeutics* 8th ed., Pergamon Press; (1990) *Remington's Pharmaceutical Sciences,* 17th ed., Mack Publishing Co., Easton, Pa.; Avis et al. (eds.) (1993) *Pharmaceutical Dosage Froms: Parenteral Medications.* Dekker, N.Y.; Lieberman et al. (eds.) (1990) Pharmaceutical Dosage Forms: Tablets Dekker, N.Y.; and Lieberman et al. (eds.) (1990) *Pharmaceutical Dosage Forms: Disperse Systems* Dekker, N.Y.

Preferably, the therapeutically effective amount is a unit dose presented in an ampoule. Alternatively, the therapeutically effective amount could be presented in a vial containing multiple doses or it could be offered in some other form. The total daily dose may be given as a single injection, a continuous infusion, or it may be divided into several smaller doses for bolus intravenous administration or administration by some other route such as intramuscular injection. Compositions of the invention may also be introduced into a patient's body by an implantable or injectable drug delivery system, e.g., Urquhart et al., Ann. Rev. Pharmacol. Toxicol. 24: 199 (1984); Lewis (Ed.), *Controlled Release of Pesticides and Pharmaceuticals* (Plenum Press, N.Y., 1981); U.S. Pat. No. 3,270,960; and the like. In appropriate circumstances, the IL-10 can also be encapsulated in a liposome.

In appropriate circumstances, multiple medications can be administered in combination. For instance, the IL-10 may be co-administered with or used in association or conjunction with other chemotherapeutic or chemopreventive agents. Examples of such agents include corticosteroids, sulphasalazine, derivatives of sulphasalazine, immunosuppressive drugs such as cyclosporin A, mercaptopurine, and azathioprine, and another cytokine. See, e.g., Thorn et al. (eds.) *Harrison's Principles of Internal Medicine,* McGraw-Hill, N.Y.; Wyngaarden et al., (eds.) *Cecil Textbook of Medicine* Saunders, *Philadelphia*; and weatherall et al. (eds.) *Oxford Textbook of Medicine* Oxford University Press, New York. The co-administration can be sequential or simultaneous. Co-administration generally means that the multiple (two or more) therapeutics are present in the recipient during a specified time interval. Typically, if a second agent is administered within the half-life of the first agent, the two agents are considered co-administered.

Further, the IL-10 can be administered in conjunction with allogenic bone marrow transplantation. The phrase "in conjunction with" means the IL-10 is administered either before, during, or after transplantation (or before, during, or after chemotherapy as the case may be). The therapy of the present invention may also be used to control acute leukemia in relapsed patients.

The broad scope of this invention is best understood with reference to the following examples, which are not intended to limit the invention to specific embodiments.

EXAMPLES

Materials and Methods

Patients

Twenty-seven patients with AML and five patients with ALL were studied. The clinical characteristics for each patient are presented in Table 1 below.

TABLE I

Clinical characteristics of acute leukemia patients

| Patient | Sex | Age | Previous hematological desease | FAB classification | CD3 | CD13 | CD14 | CD15 | CD19 | CD20 | CD33 | CD34 |
|---|---|---|---|---|---|---|---|---|---|---|---|---|
| 1 | M | 73 | Chronic myelofibrosis | AML-M2 | − | + | − | nt | − | − | + | nt |
| 2 | F | 67 | | AML-M1 | − | + | − | nt | − | − | − | − |
| 3 | F | 83 | Primary myelodysplastic syndrome | AML-M2 | − | + | − | nt | − | − | + | − |
| 4 | M | 56 | | AML-M4 | − | + | − | + | − | − | + | − |
| 5 | F | 72 | Multiple myeloma | AML-M2 | − | − | + | nt | − | − | + | − |
| 6 | F | 67 | | AML-M2 | − | + | − | nt | − | − | + | − |
| 7 | M | 30 | | AML-M2 | − | − | − | nt | − | − | + | − |
| 8 | M | 67 | Primary myelodysplastic syndrome | AML-M2 | − | + | − | nt | − | − | + | − |
| 9 | M | 82 | | AML-M4 | − | + | − | − | − | − | + | + |
| 10 | F | 37 | | AML-M5 | − | + | + | + | − | − | + | − |
| 11 | F | 54 | | AML-M2 | − | + | − | nt | − | − | + | − |

TABLE I-continued

Clinical characteristics of acute leukemia patients

| Patient | Sex | Age | Previous hematological desease | FAB classification | CD3 | CD13 | CD14 | CD15 | CD19 | CD20 | CD33 | CD34 |
|---|---|---|---|---|---|---|---|---|---|---|---|---|
| 12 | F | 64 | | AML-M2 | − | + | − | nt | − | − | − | − |
| 13 | M | 75 | Non-Hodgkins lymphoma, CHOP therapy | AML-M4 | − | + | − | nt | − | − | + | nt |
| 14 | M | 47 | | AML-M4 | − | + | + | nt | − | − | − | − |
| 15 | M | 80 | | AML-M4 | − | − | + | nt | − | − | − | − |
| 16 | F | 56 | Primary myelodysplastic syndrome | AML-M4 | − | + | + | − | − | − | + | + |
| 17 | M | 47 | | AML-M2 | − | + | + | nt | − | − | + | + |
| 18 | M | 64 | | AML-M4 | − | + | − | + | − | − | + | + |
| 19 | M | 33 | | AML-M4 | − | + | + | + | − | − | + | + |
| 20 | M | 23 | | AML-M4 | − | + | − | + | − | − | + | − |
| 21 | M | 32 | | AML-M4 | − | + | + | + | − | − | + | + |
| 22 | F | 66 | | AML-M2 | − | + | − | + | − | − | + | + |
| 23 | F | 44 | | AML-M4 | − | − | − | − | − | − | + | + |
| 24 | F | 52 | | AML-M4 | − | + | + | + | − | − | + | + |
| 25 | F | 69 | | AML-M2 | − | + | − | + | − | − | + | + |
| 26 | F | 25 | | AML-M4 | − | + | + | − | − | − | + | + |
| 27 | M | 33 | CML | CML | − | + | − | + | + | − | + | + |
| 28 | M | 84 | | ALL | − | − | − | − | + | nt | − | − |
| 29 | F | 16 | | ALL | + | − | − | − | + | + | − | − |
| 30 | F | 58 | | ALL | − | − | − | − | + | + | − | − |
| 31 | F | 29 | | ALL | + | − | − | − | + | − | − | − |
| 32 | M | 78 | | ALL | − | − | − | − | + | nt | − | + |

In Table I above, acute leukemia cells were regarded as positive when more than 20% of blast cells stained positive judged from flow cytometric analysis. For more information on the classification references used in Table I, see, e.g., Hayhoe, Blood Reviews, 2: 186–193, Scotland (Sep. 1988) and Knapp et al. Leukocyte Typing IV White cell differentiation antigens, (Oxford University Press 1989).

Culture Medium

Culture medium was RPMI 1640 with glutamine and hepes (Gibco; UK) to which was added gentamicin 100 μg/ml and 10% inactivated fetal calf serum (HiClone; USA).

Conditioned Medium

Peripheral blood mononuclear cells (PBMCs) $1 \times 10^6$/ml from a healthy individual were incubated in culture medium with phytohaemagglutinin (PHA HA 16; Wellcome, UK) 1 μg/ml for three days. The culture supernatant was then harvested and is referred to hereafter as "conditioned medium".

Cytokines

Recombinant human cytokines were used at the following concentrations in AML blast cultures: IL-2 (R&D Systems Europe, UK) 20 ng/ml; IL-3 (R&D Systems Europe; UK) 40 ng/ml; G-CSF (Hoffman La Roche; Switzerland) 100 ng/ml; GM-CSF (Sandoz; Switzerland); 100 ng/ml IL-10 was provided by Schering-Plough Corp., USA. See, e.g. Bruserud et al., Leukemia Res. 17: 507 (1993), Lemoll etal., Leukemia 5: 386 (1991); Assano et al., Blood 72: 1682 (1988).

Cell Preparation

PBMCs were isolated by density gradient separation (Ficoll-Hypague, NyCoMed, Norway; specific density 1.077). To reach a high percentage of leukemia blasts among these mononuclear cells (>95%), only patients with a high number of blast cells in peripheral blood were included in the study. Cells were stored frozen in liquid nitrogen. See Bruserud, Acta Oncol. 31: 53 (1992) which describe, inter alia, the methods of freezing and thawing that were used.

Proliferation Assay

As described in detail in Bruserud et al., Leukemia Res. 17: 507 (1993) and Bruserud, Acta Oncol 31: 53 (1993), acute leukemia blast cells $5 \times 10^4$/well were cultured in flatbottomed microtiter plates (Costar; USA), each well containing 150 μl medium. Cells were incubated at 37° C. in a humidified atmosphere of 5% $CO_2$. $^3$H-thymidine 37 kBq/well (TRA 310; Amersham, UK) was added 24 hours before cultures were harvested and nuclear radioactivity measured by liquid scintillation counting.

Colony-Forming Assay

AML blast cells (2×106/well) were cultured in 200 μl culture medium in each well of 24 wells tissue culture plates (Costar, USA). All cultures were performed in duplicates. The number of colonies exceeding 20 cells were counted after 9 days of culture.

Analysis of Cytokine Production

As described in Bruserud et al., Leukemia Res. 19: 15 (1995), AML blast cells $1 \times 10^6$/ml were cultured in 24 well tissue culture plates (Costar, USA), each well containing 2 ml of medium. Cultures were incubated for 48 hours before supernatants were harvested. Cytokine secretion was analyzed by determining cytokine concentrations in the culture supernatants. Concentrations IL-1α, IL-1β,IL-1RA, IL-4, IL-6, TNFα and GM-CSF were determined using ELISA assays (Quantlkine ELISA kits, R&D System Europe; UK). All assays were performed strictly according to the manufacturer's instructions. Briefly, standard samples and dilutions of supernatant were prepared in culture medium. Standard curves were determined using the mean of duplicate determinations, and differences between duplicates were generally <10% of the mean. Supernatants were analyzed at a dilution resulting in a measured concentration within the range of the standard curve. The minimal detectable concentrations for each assay were IL-1α 0.3 pg/ml, IL-1 β 0.3 pg/ml, IL-1RA 6.5 pg/ml, IL-4 3 pg/ml, IL-6 0.35 pg/ml, TNFα 4.8 pg/ml and GM-CSF 1.5 pg/ml.

Presentation of the Data

Proliferation assays were performed in triplicates. The median counts per minute (cpm) of triplicate cultures were used for statistical analysis. Significant proliferation was defined as $^3$H-thymidine incorporation corresponding to >1000 cpm and exceeding the negative control by at least 3 standard deviations (SD). A significant increase/decrease was defined as either (i) an alteration of at least 1500 cpm, and the alteration exceeding 10% of responses in control cultures; or (ii) conversion from no proliferation to significant proliferation. For statistical analysis the Willcoxon's test for paired samples was used (see, e.g., Wonnacott and Wonnacott, Introductory statistics, Third Edition, Wiley 1977), and in these statistical calculations the median cpm was used for the proliferation assay.

Results

Effect of IL-10 on Spontaneous in vitro Proliferation of AML Blast Cells

Figure 1A:
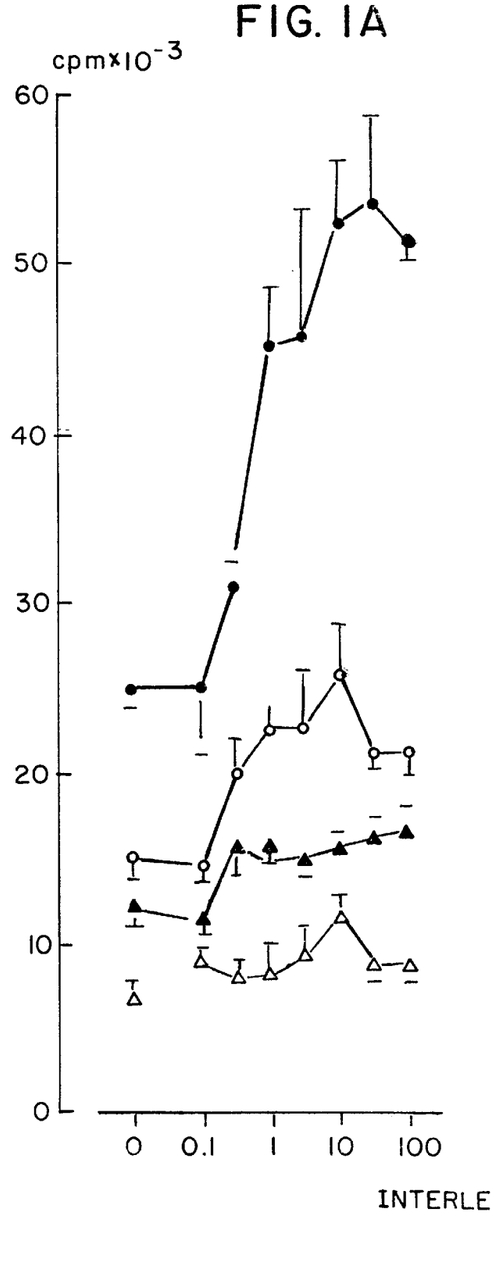
FIGS. 1A and 1B are graphical representations showing the effect of IL-10 on AML blast proliferation as a function of IL-10 concentration for two particular patients (Patient No. 2 in FIG. 1A, Patient No. 15 in FIG. 1B). Specifically, these figures show the results when testing spontaneous proliferation (open triangles), and also when testing AML blast proliferation in the presence of G-CSF (closed circles), GM-CSF (open circles) and IL-3 (closed triangles). Proliferation was tested as $^3$H-thymidine incorporation after seven days of culture, and the results are presented as mean cpm±SD of triplicate cultures.
Figure 1B:
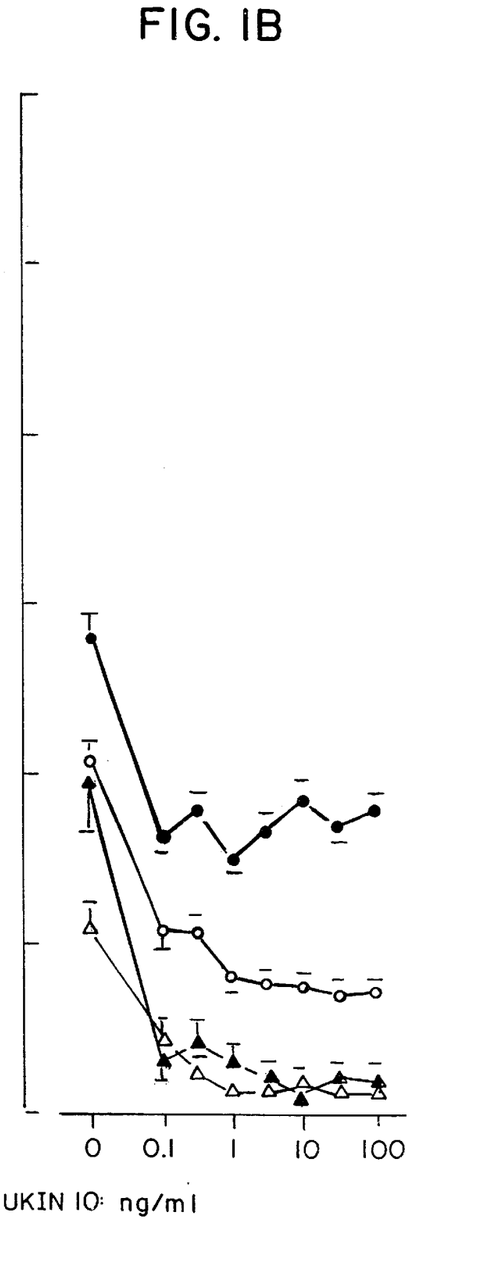

AML blast cells from 16 patients (Patients 1 through 16) were cultured in vitro in medium alone and in the presence of various concentrations of IL-10 (range 100–0.01 ng/ml), and $^3$H-thymidine incorporation was assayed after seven days. For seven patients, no proliferation was seen when AML blasts were cultured in medium alone. For the nine patients showing spontaneous in vitro proliferation, IL-10 showed dose-dependent effects on proliferation with a plateau at concentrations exceeding 1 ng/ml. The results for two patients (Patient No. 2 and Patient No. 15) are shown in FIGS. 1A and 1B, respectively (open triangles).

Figure 2A:
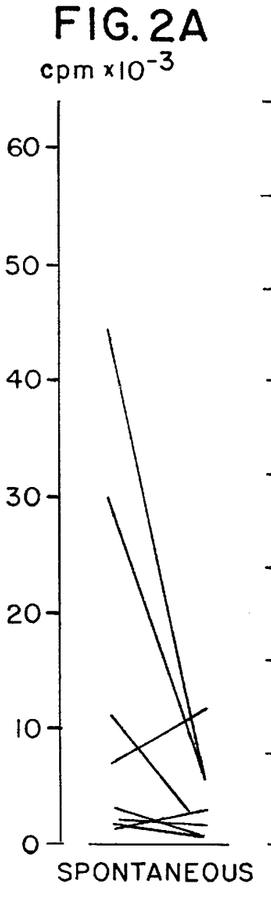

FIG. 2A is graphical representation showing the effect of IL-10 (10 ng/ml) on spontaneous AML blast proliferation for the nine patients whose cells had previously shown proliferation when incubated in medium alone. The left side of FIG. 2A shows proliferation (as demonstrated by $^3$H-thymidine incorporation) in cultures without IL-10, while the right side of this figure shows proliferation in cultures with IL-10 (10 ng/ml). As can be seen from this data, IL-10 caused a small, but statistically significant, increase in AML blast proliferation for two of the nine selected patients (Patients 1 and 2). For the remaining seven patients, IL-10 resulted in a dose-dependent inhibition of AML blast proliferation (p=0.049). For six patients (patients 1, 2, 5, 10, 14, 16) the effects of IL-10 were reproduced in repeated experiments (data not shown).

Effect of IL-10 on Cytokine-dependent in vitro Proliferation of AML Blast Cells

G-CSF Dependent Proliferation

Figure 2B:
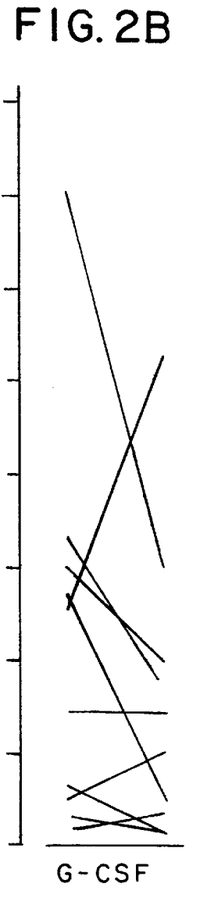

AML blast cells from Patients 1–16 were cultured with G-CSF (100 ng/ml) and different concentrations of IL-10 (range 100–0.01 ng/ml). $^3$H-thymidine incorporation was then assayed after 7 days. G-CSF alone caused significant AML blast proliferation for 10 patients, and for 9 of these 10 patients IL-10 showed a dose-dependent effect on AML blast proliferation with a plateau at concentrations exceeding 1 ng/ml. The results for Patients 2 and 15 are shown in FIGS. 1A and 1B, respectively (closed circles). When comparing the overall results (IL-10 at concentrations of from 100–0.1 ng/ml), IL-10 increased G-CSF proliferation for only four patients (Patients 2, 8, 13 and 16), whereas for six patients proliferation was either unaltered or decreased. The results when testing IL-10 at the concentration of 10 ng/ml are presented in FIG. 2B, and as can be seen in the figure, increased proliferation was seen for only 3 of the 10 patients.

GM-CSF Dependent Proliferation

Figure 2C:
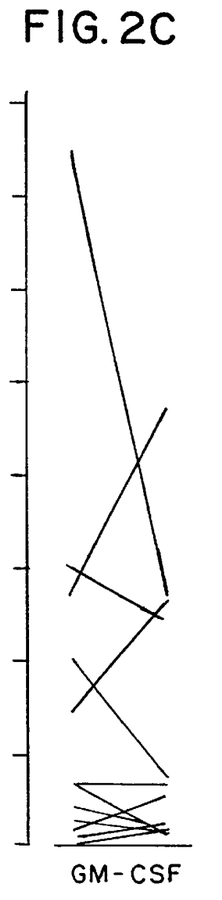

AML blasts from 16 patients (patients 1 through 16) were cultured with GM-CSF (100 ng/ml) with significant proliferation seen for 12 of these patients. IL-10 (tested at concentrations ranging from 100–0.01 ng/ml) increased proliferation for 5 patients (patients 2, 6, 8, 13, 16), whereas unaltered or decreased proliferation was seen for 7 patients. (See FIG. 2C). When IL-10 significantly altered blast proliferation, this effect seemed dose-dependent with a maximum at concentrations exceeding 1 ng/ml. The results for Patients 2 and 15 are shown in FIGS. 1A and 1B, respectively (open circles).

IL-3 Dependent Proliferation

Figure 2D:
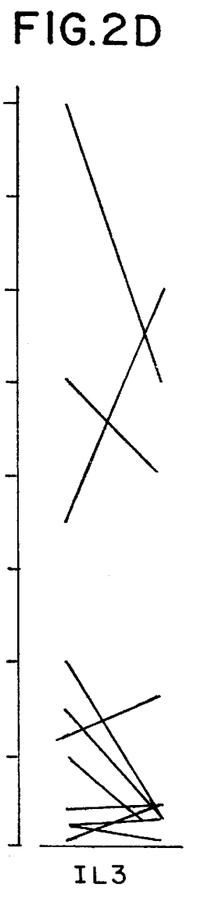

AML blast cells were cultured with IL-3 (20 ng/ml), and significant proliferation was then seen for 11 of the 16 patients tested. (Data not shown). IL-10 (tested at concentrations ranging from 100–0.003 ng/ml) increased proliferation for three patients (Patients 2, 6 and 9) out of the 11 patients tested, whereas for eight patients proliferation was either unaltered or decreased. (See FIG. 2D). When IL-10 caused a significant alteration of AML blast proliferation, this effect seemed dose-dependent with a plateau at concentrations exceeding 1 ng/ml. The results for Patients 2 and 15 are shown in FIGS. 1A and 1B, respectively. For six patients (Patients 1, 2, 5, 10, 14, 16), the effects of IL-10 on cytokine-dependent proliferation (G-CSF, GM-CSF, IL-3) was reproduced in repeated experiments (data not shown).

Effect of IL-10 on PHA-Stimulated Proliferation of Normal PBMCs

In order to further demonstrate that the anti-proliferative effect of IL-10 was not due to a toxic effect of the IL-10 preparation on cells in vitro, normal PBMCs (10 healthy individuals tested) were stimulated with optimal concentrations of phytohaemagglutinin and proliferation assayed after three days. IL-10 (20 ng/ml) did not alter PBMC proliferation. (Data not shown).

AML Blast Proliferation is Inhibited after Preincubation with IL-10

Figure 3A:
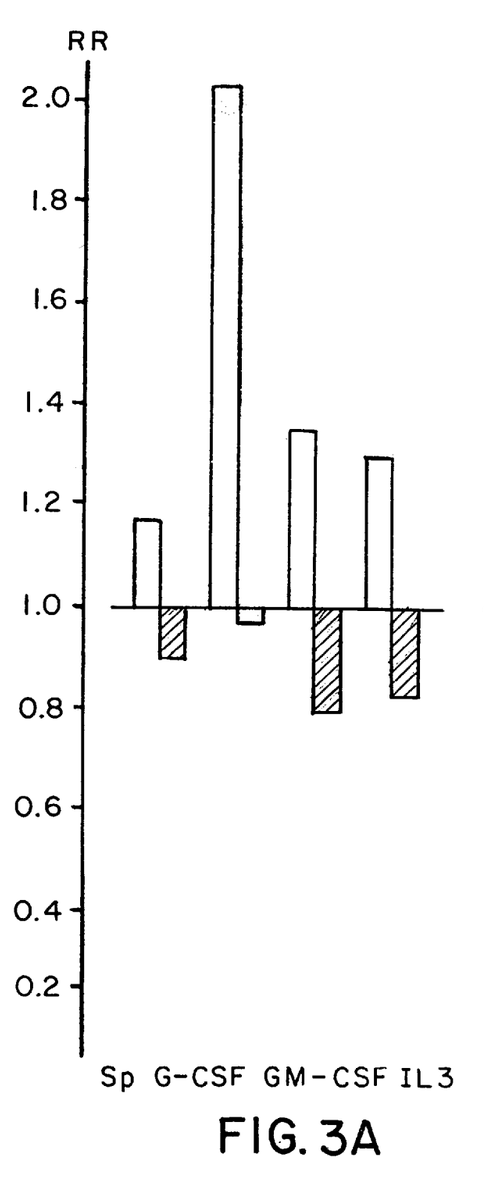
Figure 3B:
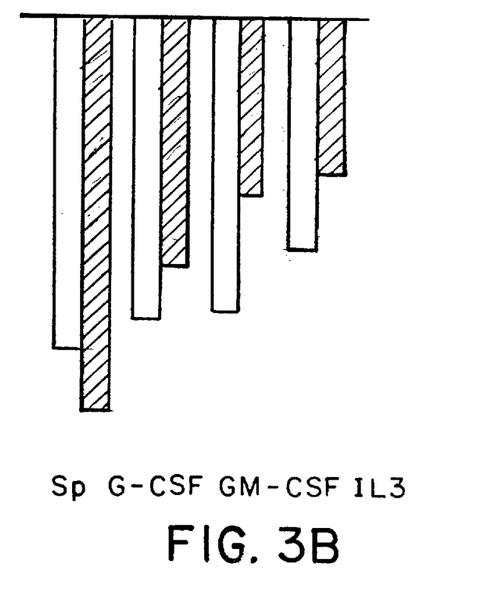

AML blast cells were incubated in culture medium with and without IL-10 (100 and 20 ng/ml). After 48 hours, cells were washed, the cell concentrations adjusted, and the blast cells cultured for additional five days before $^3$H-thymidine incorporation was assayed. During the last five days, AML cells were cultured in medium alone and with G-CSF, GM-CSF, G-CSF+GM-CSF or IL-3. Ten patients were investigated; the results for Patient 2 are presented in FIG. 3A and the results for Patient 15 are presented in FIG. 3B. Preincubation with IL-10 either did not significantly alter proliferation or decreased proliferation when AML blast cells were cultured in medium alone or with IL-3 during the last 5 days. The inhibition of spontaneous proliferation was seen even for patients who showed increased proliferation when IL-10 was present during the whole culture period. (See FIG. 3A). A small increase in cytokine-dependent AML blast proliferation after IL-10 preincubation could still be seen for a few patients when the blasts were cultured with G-CSF (1/11), GM-CSF (1/11) and G-CSF+GM-CSF (3/11) during the last five days of culture, but this increase was lower than for AML blast cells cultured with IL-10 for the whole culture period. Four patients were tested in repeated experiments (patients 1, 2, 11, 13), and the inhibitory effect on AML blast proliferation of IL-10 preincubation could then be reproduced (data not shown).

Effect of IL-10 on in vitro Colony Formation of AML Blast Cells

To investigate whether IL-10 could inhibit growth of clonogenic AML cells, the blasts from 5 patients were cultured with a hematopoietic growth factor in a colony forming assay. Cultures were prepared with and without IL-10 (20 ng/ml). For all patients blast cells were cultured with the cytokine causing the strongest proliferative response judged from the $^3$H-thymidine assay. The results are presented in Table 2 below. As can be seen from the data, IL-10 inhibited colony formation for all 5 patients investigated.

TABLE II

The Effect of IL-10 on AML Blast Cell Colony Formation.

| | | Colony Formation** | |
|---|---|---|---|
| Patient | Cytokine | Culture medium alone | Culture medium + IL10 20 ng/ml |
| 9 | G-CSF | 29.5 ± 2.1 | 19.0 ± 2.8 |
| 10 | IL-3 | 8.0 ± 2.8 | 0 |
| 14 | G-CSF | 7.5 ± 0.7 | 4.5 ± 0.7 |
| 15 | G-CSF | 16.0 ± 4.2 | 3.5 ± 2.1 |
| 16 | IL-3 | 8.0 ± 2.8 | 0 |

**The results are presented as the mean number of colonies per well ± SD. All tests were performed in duplicate.

Effect of IL-10 on in vitro Proliferation of ALL Blast Cells

Figure 4:
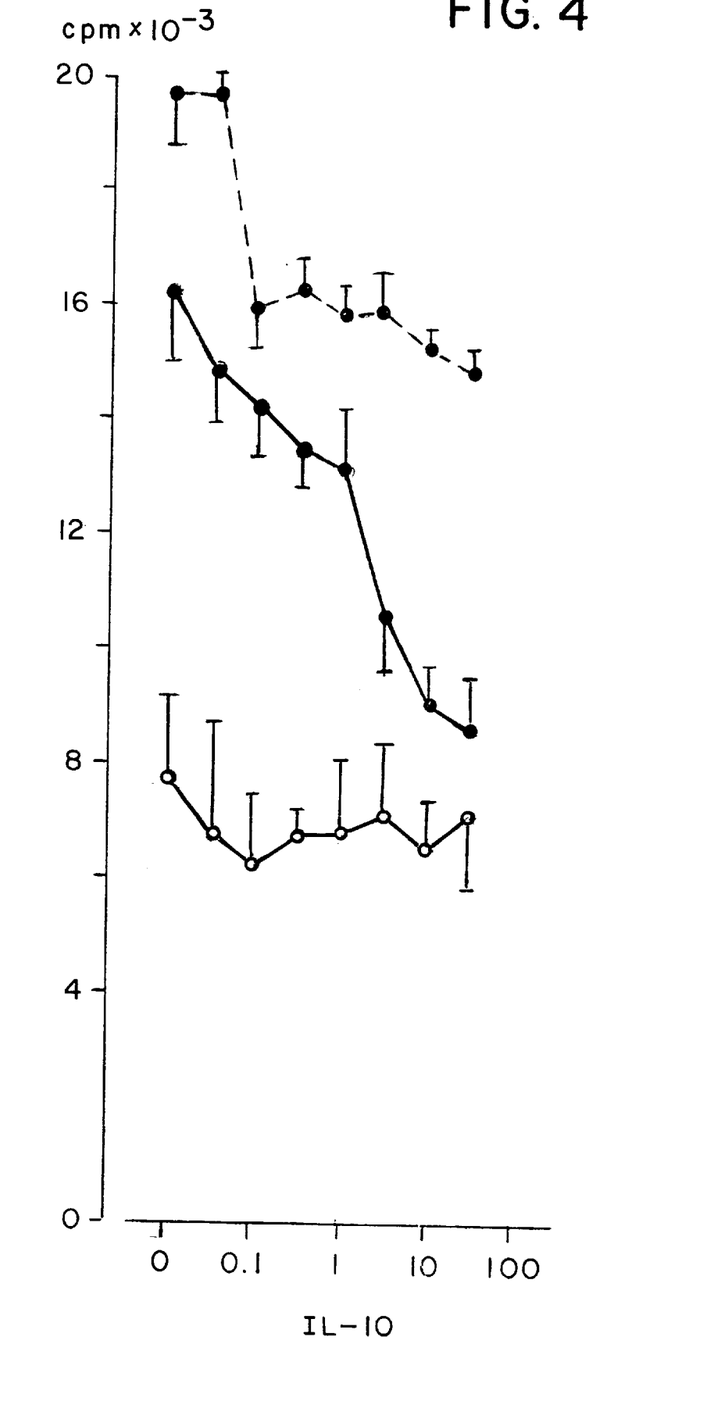
FIG. 4 is a graphical representation showing the effect of IL-10 on growth factor dependent proliferation of blast cells derived from three different ALL patients. The results are presented as mean cpm±SD of triplicate cultures.

Blast cells derived from 5 patients with ALL were cultured in vitro with and without IL-10 (range 100–0.03 ng/ml) in the presence of 10% conditioned medium and IL-2 20 ng/ml, and $^3$H-thymidine incorporation was assayed after five days. IL-10 caused a dose-dependent inhibition of ALL blast proliferation for all patients investigated. The results for three of the patients are presented in FIG. 4. Specifically, FIG. 4 shows the effect of IL-10 on growth factor dependent proliferation of blast cells derived from ALL patients 28 (closed circles), 29 (closed triangles), and 30 (open circles). The results are presented as mean cpm±SD of triplicate cultures.

Effect of IL-10 on Cytokine Secretion from AML Blast Cells

Figure 5A:
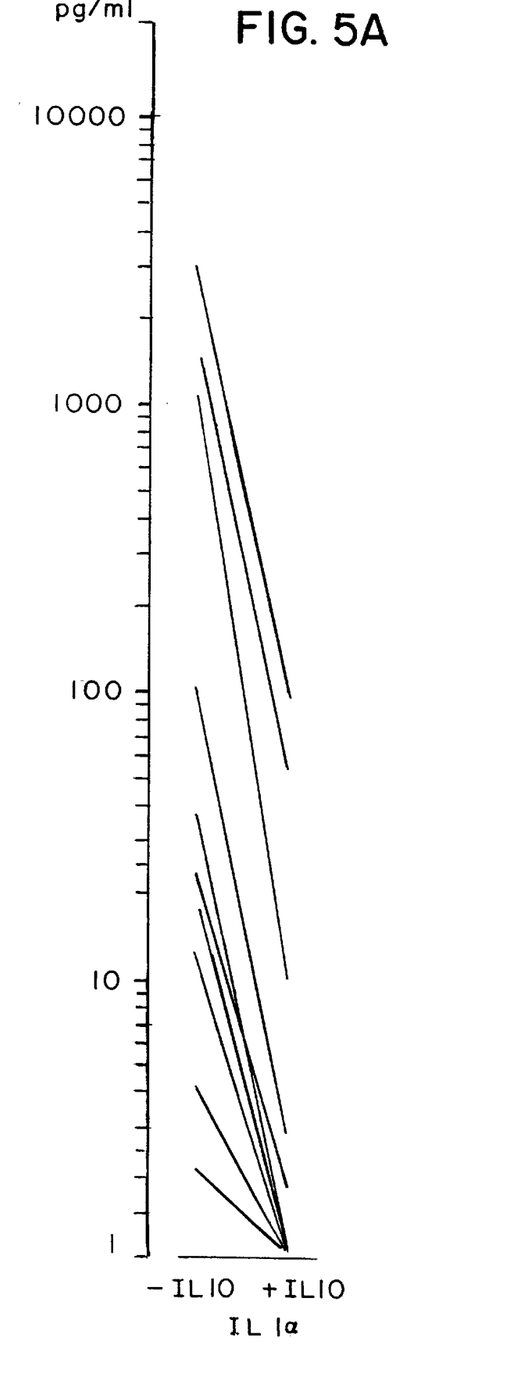
FIGS. 5A and 5B are graphical representations showing the effect of IL-10 on secretion of IL-1α (FIG. 5A, n=10) and IL-1β (FIG. 5B, n=27) from AML blast cells. The results are presented as IL-1 concentrations in culture supernatants from AML blast cells cultured with and without IL-10 (20 ng/ml) for 48 hours.
Figure 5B:
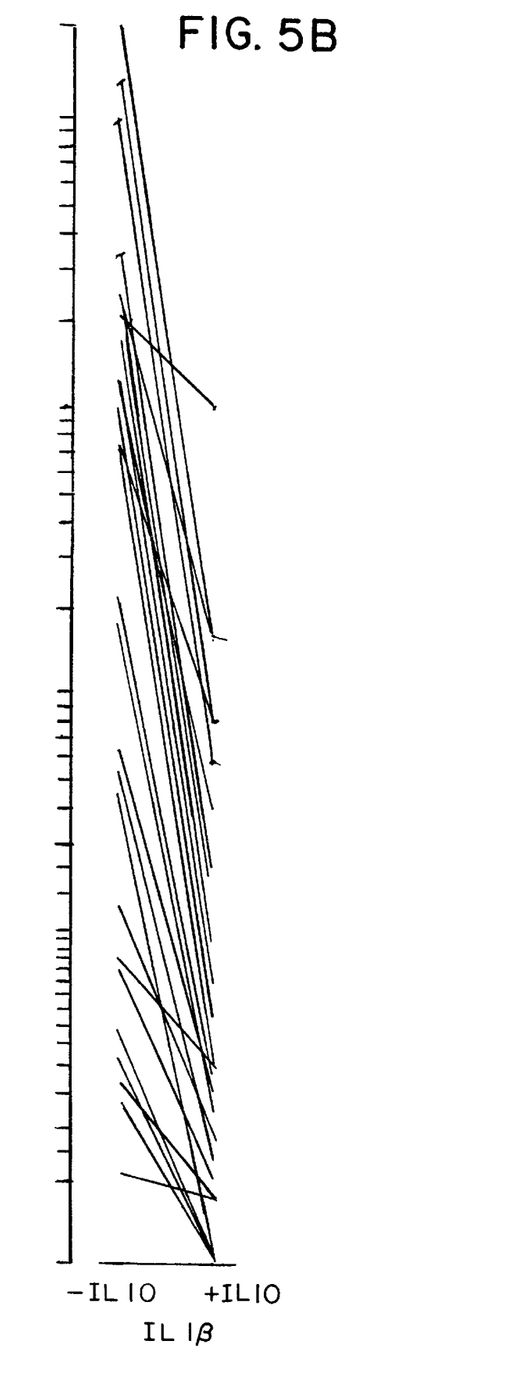

AML blast cells were cultured in vitro for 48 hours, and concentrations of various cytokines were determined in the culture supernatants. Cells were cultured with and without IL-10 (20 ng/ml). The overall results for IL-1 secretion are presented in FIGS. 5A and 5B as IL-1 concentrations in culture supernatants from the AML blast cells. Specifically, FIG. 5A shows the effect of IL-10 on secretion of IL-1α in 10 cases (Patients 18–27, p=0.01); FIG. 5B shows the effect of IL-10 on secretion of IL-1β, for Patients 1–27 (p<0.0005). In the absence of IL-10, both IL-1α and IL-1β secretion could be detected for all patients examined. In contrast, the presence of IL-10 inhibited secretion of IL-1α and IL-1β for all patients investigated.

Figure 6A:
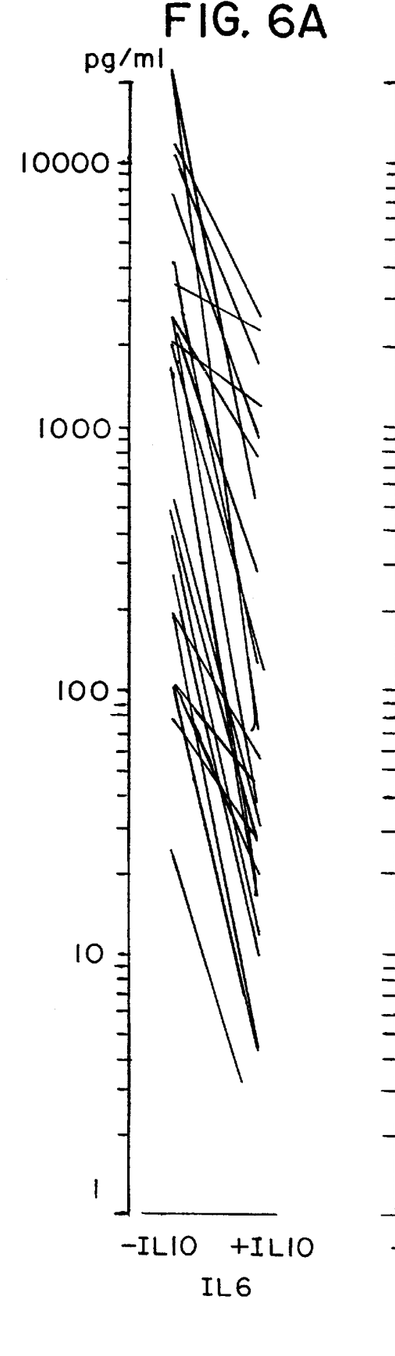
FIGS. 6A, 6B, and 6C are graphical representations showing the effect of IL-10 on secretion of, respectively, IL-6 (FIG. 6A, n=25), TNFα (FIG. 6B, n=25), and GM-CSF (FIG. 6C, n=18) from AML blast cells. The results are presented as cytokine concentrations in supernatants from AML blast cells cultured with and without IL-10 (20 ng/ml) for 48 hours.
Figure 6B:
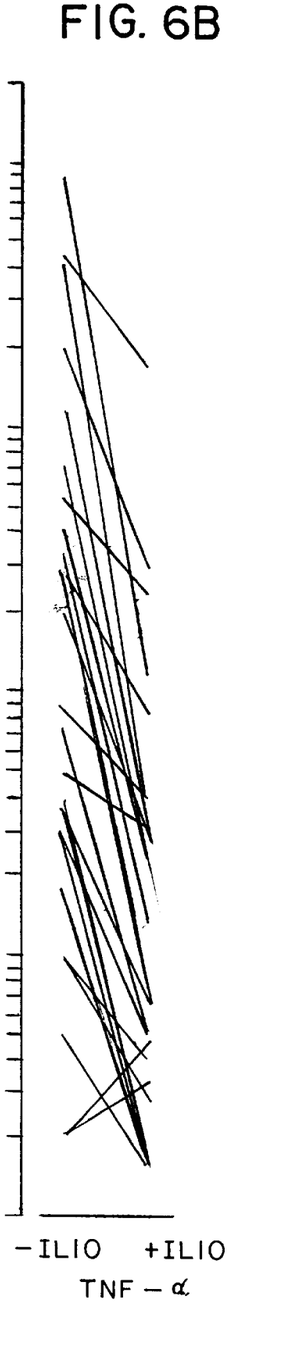
Figure 6C:
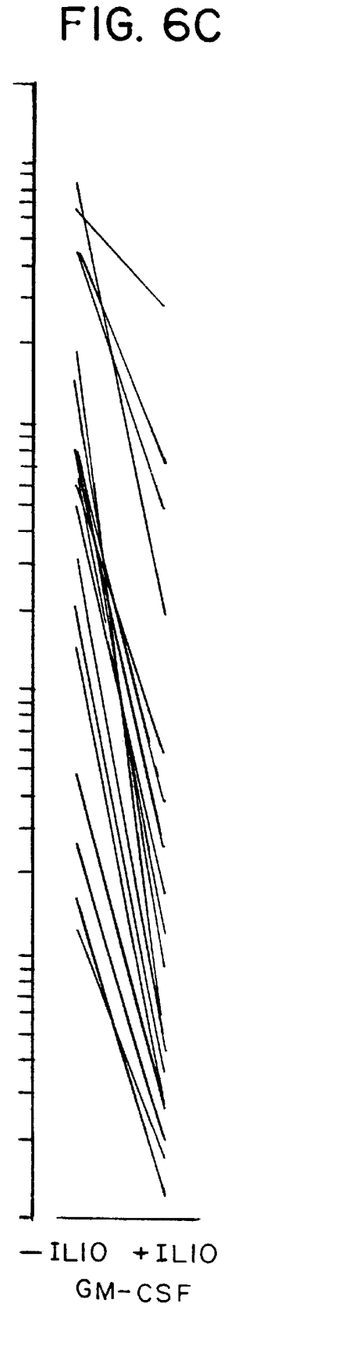

AML blast secretion of IL-6, TNFα and GM-CSF was also studied as described above. The results are presented in FIGS. 6A, 6B and 6C as cytokine concentrations in supernatants from AML blast cells cultured with and without IL-10 (20 ng/ml) for 48 hours. IL-6 could be detected for all patients tested (patients 1–20 and 22–26) when cells were cultured in medium alone, and as shown in FIG. 6A, IL-10 significantly decreased IL-6 concentrations (n=25; p<0.0005). TNF α could be detected for 25 out of 27 patients (patients 1–27) when cells were cultured in medium alone, and FIG. 6B shows that IL-10 significantly decreased TNFα secretion (n=25; p<0.001). GM-CSF was detected for 18 patients out of 21 patients studied, but as shown in FIG. 6C, IL-10 caused decreased secretion of GM-CSF for all of these 18 patients (n=18; p<0.0005).

For six patients secretion of IL-1β, IL-6 and TNFα was tested in repeated experiments, and the inhibitory effect of IL-10 could then be reproduced (see Table III below).

TABLE 3

The effect of IL-10 in vitro cytokine secretion by leukemic PBMC and enriched AML blasts

| | | IL 10 | Cytokine[1] | | |
|---|---|---|---|---|---|
| Patient | AML cells | 20 mg/ml | IL 1β | IL 6 | TNFα |
| 1 | PBMC | − | nd[2] | nd | nd |
| | | + | nd | nd | nd |
| | Enriched blasts | − | nd | nd | nd |
| | | + | nd | nd | nd |
| 2 | PBMC | − | 1220 ± 28 | 996 ± 21.2 | 300 ± 17 |
| | | + | nd | 16 ± 1.4 | nd |
| | Enriched blasts | − | 495 ± 21 | 285 ± 14.2 | 172 ± 0 |
| | | + | nd | 11 ± 1.4 | nd |
| 5 | PBMC | − | 145 ± 0 | 3750 ± 70.7 | 4320 ± 113 |
| | | + | nd | nd | 14.2 ± 3.1 |
| | Enriched blasts | − | 510 ± 42 | 4050 ± 70.7 | 4500 ± 141 |
| | | + | nd | nd | nd |
| 10 | PBMC | − | nd | 87.5 ± 1.4 | 584 ± 22.6 |
| | | + | nd | 10.5 ± 1.4 | 82 ± 2.8 |
| | Enriched blasts | − | nd | 81 ± 1.4 | 568 ± 11.3 |
| | | + | nd | 4.4 ± 2.8 | 36.2 ± 1.4 |
| 14 | PBMC | − | 220 ± 28 | 636 ± 17.0 | nd |
| | | + | nd | 37 ± 7.1 | nd |
| | Enriched blasts | − | 45 ± 13 | 170 ± 2.8 | nd |
| | | + | nd | 9.2 ± 0.6 | nd |

TABLE 3-continued

The effect of IL-10 in vitro cytokine secretion by leukemic PBMC and enriched AML blasts

| Patient | AML cells | IL 10 20 mg/ml | Cytokine[1] | | |
|---|---|---|---|---|---|
| | | | IL 1β | IL 6 | TNFα |
| 16 | PBMC | − | 300 ± 14 | 1580 ± 28 | 780 ± 28.3 |
| | | + | nd | nd | nd |
| | Enriched blasts | − | 455 ± 21 | 1660 ± 141 | 640 ± 28.3 |
| | | + | 80 ± 1.4 | 1230 ± 42.4 | 61 ± 1.4 |

[1]Cytokine secretion was analysed by culture of leukemic PBMC or enriched blasts in culture medium with and without IL 10 20 ng/ml for 48 hours before supernatants were collected and cytokine concentrations determined. The results are expressed as mean concentration (pg/ml) ± standard deviation of duplicte determinations.
[2]nd: not detectable For patients 18–27 proliferation was assayed in cultures with and without IL-10 together with the cytokine determinations. In these experiments AML blast cells were cultured at the concentration $1 \times 10^6$/ml, $^3$H-thymidine was added after 24 hours, and cultures were harvested after 48 hours. For cultures without IL-10 significant proliferation could not be detected for patients 21, 23 and 25, whereas IL-10 inhibited blast proliferation for all seven patients showing significant proliferation (n=7; mean inhibition 26%; range 1–63%).

Many modifications and variations of this invention will be apparent to those skilled in the art. The specific embodiments described herein are offered by way of example only, and the invention is not to be construed as limited thereby.

What is claimed is:

1. A method for treating an acute leukemia in a mammal, comprising administering a therapeutically effective amount of interleukin-10 to said mammal.

2. The method of claim 1, wherein the acute leukemia is acute myelogenous leukemia.

3. The method of claim 1, wherein the acute leukemia is acute lymphocytic leukemia.

4. The method of claim 1, wherein the interleukin-10 is selected from the group consisting of viral interleukin-10 and human interleukin-10.

5. The method of claim 1, further comprising administering a therapeutically effective dose of a second therapeutically active agent.

6. The method of claim 5, wherein the second therapeutically active agent is a cytokine.

7. The method of claim 5, wherein the second therapeutically active agent is a chemotherapeutic agent.

8. The method of claim 1, wherein the interleukin-10 is administered intravenously.

9. The method of claim 1, wherein the interleukin-10 has an antiproliferative effect on acute leukemia blast cells which persists after the administration of interleukin-10 is stopped.

10. The method of claim 1, wherein the effective amount of interleukin-10 is between about 10 micrograms to about 200 micrograms per kilogram per day.

11. The method of claim 1, wherein the amount of interleukin-10 is between about 25 micrograms to about 100 micrograms per kilogram per day.

12. The method of claim 1, wherein the interleukin-10 is administered in conjunction with allogenic bone marrow transplantation.

13. A method for inhibiting proliferation of acute leukemia blast cells, comprising administering a therapeutically effective dose of interleukin-10 to a mammal suffering from an acute leukemia.

14. The method of claim 13, wherein the inhibition persists after the administration of interleukin-10 is stopped.

15. The method of claim 13, wherein the acute leukemia is acute myelogenous leukemia.

16. The method of claim 13, wherein the acute leukemia is acute lymphoblastic leukemia.

* * * * *